(12) United States Patent
Gardiner et al.

(10) Patent No.: US 7,943,183 B2
(45) Date of Patent: May 17, 2011

(54) COMPOSITIONS AND METHODS FOR INCREASING METABOLISM, THERMOGENESIS AND/OR MUSCULAR DEFINITION

(76) Inventors: Paul T. Gardiner, Mississauga (CA); Marvin A. Heuer, Mississauga (CA)

( * ) Notice: Subject to any disclaimer, the term of this patent is extended or adjusted under 35 U.S.C. 154(b) by 1343 days.

(21) Appl. No.: 11/485,713

(22) Filed: Jul. 12, 2006

(65) Prior Publication Data

US 2007/0014878 A1   Jan. 18, 2007

Related U.S. Application Data

(63) Continuation-in-part of application No. 11/385,144, filed on Mar. 20, 2006, now abandoned.

(60) Provisional application No. 60/663,396, filed on Mar. 18, 2005.

(51) Int. Cl.
*A61K 36/28* (2006.01)
*A61K 36/48* (2006.01)

(52) U.S. Cl. ......................................... 424/764; 424/757

(58) Field of Classification Search ........................ None
See application file for complete search history.

(56) References Cited

U.S. PATENT DOCUMENTS

| | | | |
|---|---|---|---|
| 6,174,542 B1 | 1/2001 | Hinton et al. | |
| 6,277,396 B1 * | 8/2001 | Dente | 424/439 |
| 6,869,621 B2 | 3/2005 | Hwang et al. | |
| 2004/0071681 A1 * | 4/2004 | Muller | 424/94.1 |
| 2005/0008690 A1 | 1/2005 | Miller | |
| 2005/0025844 A1 | 2/2005 | Boldt | |
| 2005/0112212 A1 | 5/2005 | Organ et al. | |
| 2005/0256192 A1 | 11/2005 | Gardiner | |

FOREIGN PATENT DOCUMENTS

| | | | |
|---|---|---|---|
| EP | 1502598 | | 2/2005 |
| FR | 2183529 A | * | 1/1974 |
| JP | 2002 095940 | | 4/2003 |
| WO | 03090673 | | 11/2003 |
| WO | 2005107735 | | 11/2005 |

OTHER PUBLICATIONS

Bishop. May 2003. Web archive date Feb. 11, 2005 Retrieved from the internet. <http://web.archive.org/web/20050211073010/http://rossbishop.com/Articles/Monthly0305_DepressionAminos.htm>. Retrieved on Sep. 30, 2010. pp. 1-6.*
Viable-herbal.com. Web archive date. Jan. 23, 2000. <http://web.archive.org/web/20000124113842/http://viable-herbal.com/herbology1/herbs42.htm>. Retrieved on Oct. 1, 2010.*
Rowley. Preliminary Evidence on Pikamilone. Joe Weider's Muscle & Fitness. Aug. 1997; 58, 8. p. 166.*
Norberg et al. A Novel Insulin-releasing Substance, Phanoside, From the Plant Gynostemma Pentaphyllum. The Journal of Biological Chemistry.vol. 279, No. 4, Oct. 1, 2004. pp. 41361-41367.*
Liquorice. Web archive date Jul. 26, 2004. Retrieved from the internet. <http://web.archive.org/web/20040726103323/http://en.wikipedia.org/wiki/Liquorice>. Retrieved on Oct. 1, 2010. 1 page.*
Pierce. Practical Guide to Natural Medicines. Harper Collins. 1999. p. 122.*
Hemat. Principles of Orthomolecularism. Urotext. 2003. p. 177.*
Berube-Parent S. et al., "Effects of encapsulate green tea and Guarana extracts containing a mixture of epigallocatechin-3-gallate and caffeine on 24h energy expenditure and fat oxidation in men", Br. J. Nutr. Sep; 94(3):432-6.
International Search Report, PCT/CA2006/00041, mailed Jun. 22, 2006.
Search report for EP application serial No. 06752895.0, Jul. 21, 2009 5 pages.
Hook L, et al. "Evaluation of Dandelion for diuretic activity and variation in potassium content" Int. J. Pharmacog 1993. vol. 31, No. 1, pp. 29-34.
Kreydiyyeh SI, Usta J. "Diuretic effect and mechanism of action of parsley" J Ethnopharmacol. Mar. 2002;79(3):353-7. ISSN 03788741.

* cited by examiner

*Primary Examiner* — Patricia Leith
*Assistant Examiner* — Melenie McCormick

(57) ABSTRACT

Compositions and methods for administering the same to humans are provided for the promotion of increasing a person's natural metabolic rate, increasing thermogenesis, increasing training intensity, increasing muscular definition, and/or decreasing water retention. Said compositions may comprise, green tea extract, anhydrous caffeine, *theobroma cocao* extract, oolong tea extract, white tea extract, guarana, yerba maté powder, dandelion root extract, juniper berry powder, parsley powder *garcinia cambogia* extract, cayenne pepper powder extract, n-acetyl-l-tyrosine, quercetin dehydrate, *gynostemma pentaphyullum* extract, vinpocetine and optionally thiamin, pyridoxine, picamilone, xanthinol nicotinate, *garcinia cambogia* extract and niacin.

2 Claims, No Drawings

COMPOSITIONS AND METHODS FOR INCREASING METABOLISM, THERMOGENESIS AND/OR MUSCULAR DEFINITION

RELATED APPLICATIONS

This application is a continuation-in-part application of Applicant's U.S. patent application Ser. No. 11/385,144, filed on Mar. 20, 2006 now abandoned. Moreover, this application claims the benefit of priority to Applicant's co-pending U.S. patent application Ser. No. 11/385,144, and to U.S. Provisional Patent Application No. 60/663,396, filed Mar. 18, 2005, the disclosures of which are hereby incorporated in their entirety by reference.

FIELD OF THE INVENTION

The present invention relates to compositions and methods for increasing a person's natural metabolic rate, increasing thermogenesis or decreasing water retention.

SUMMARY OF THE INVENTION

In one aspect, the present invention comprises a composition of a first combination that comprises green tea extract, anhydrous caffeine, and guarana powder; a second combination that comprises dandelion root extract, and juniper berry powder; and a third combination that comprises N-acetyl-L-tyrosine, and *gynostemma pentaphyullum*. Additionally, the present invention may also comprise thiamin, pyridoxine, niacin, quercetin dehydrate, cayenne pepper powder, oolong tea extract, white tea extract, *theobroma cocao* extract, vinpocetine, yerba mate leaf powder, parsley powder extract, picamilone, and xanthinol nicotinate. The present invention may also comprise a combination that comprises Dandelion Powder, N-Acetyl-L-Tyrosine, *Gynostemma Pentaphyullum* and Picamilone. In another aspect, the present invention provides methods for increasing the natural metabolic rate, burning calories, increasing thermogenesis and decreasing water retention in a subject utilizing the invention. In another aspect, the present invention provides methods of reducing body fat mass leading to weight loss and improving muscular definition in subjects. In another aspect, the present invention provides methods of decreasing water retention and stimulating diuretic effects, thereby improving muscular definition.

DETAILED DESCRIPTION OF THE INVENTION

The present invention, according to one embodiment, provides a composition for increasing a subject's natural metabolic rate and/or decreasing water retention, thus reducing a subject's body fat mass leading to weight loss and improving visible muscular definition. Certain embodiments of the present invention include diet supplements. According to other embodiments of the present invention, there is provided a composition that reduces body fat mass leading to weight loss, thus improving muscular definition. In one embodiment the present invention may allow a subject to burn more calories than the subject would otherwise burn (dramatically increasing thermogenesis), thereby reducing body fat mass leading to weight loss.

In another embodiment the present invention provides compositions and methods that decrease water retention in subjects. For example, the composition and method may provide a diuretic effect causing a person to retain less water than the person would otherwise retain, thereby providing weight loss and improving muscular definition.

In certain embodiments of the present invention, a composition and related methods comprise:

a first combination of one or more of *theobroma* extract, green tea extract, oolong tea extract, white tea extract, anhydrous caffeine, niacin, and yerba mate extract, and guarana extract;

a second combination of one or more of dandelion root extract, juniper berry powder, parsley powder (leaf) and cayenne pepper powder;

a third combination of one or more of N-acetyl-L-tyrosine, *gynostemma pentaphyullum* extract, and vinpocetine. Additionally, the present invention may also comprise thiamin, pyridoxine, picamilone, *garcinia cambogia*, and/or xanthinol nicotinate. In another embodiment, the present invention may further comprise ingredients such as, thiamin or any salts or esters thereof, niacin, xantinol nicotinate, picamilone, and pyridoxine or a salt thereof in any of its pharmaceutically acceptable forms.

The present invention may also comprise a fourth combination that comprises Dandelion Powder, N-Acetyl-L-Tyrosine, *Gynostemma Pentaphyullum* and Picamilone.

Compounds according to the present invention have been shown to have thermogenic effects. Catechin epigallocatechin-3-gallate (EGCG), a component of green tea, has been shown to possess the ability to give to rise to thermogenic effects. In one study (Berube-Parent S, Pelletier C, Dore J, Tremblay A. (2005) "Effects of encapsulated green tea and Guarana extracts containing a mixture of epigallocatechin-3-gallate and caffeine on 24 h energy expenditure and fat oxidation in men." Br J Nutr. September; 94(3):432-6.) the energy expenditure and fat oxidation over a 24-hour time period employing components of the present invention was observed. Fourteen subjects took part in a randomized, placebo-controlled, double blind, crossover study. Each subject was tested 5 times in a metabolic chamber to measure 24-hour energy expenditure, substrate oxidation and blood pressure. During each stay, the subjects ingested a placebo or capsules containing components of the present invention 30 minutes before standardized meals. It was found that 24-hour energy expenditure increased significantly by about 750 kJ within all the treatment groups compared to placebo. This study found an increase in the 24-hour energy expenditure in the treatment groups. The resultant increase in energy expenditure via treatment with components comprising the present invention leads to an increase in the natural metabolic rate, the burning of calories, and an increase in thermogenesis.

Where the composition is in the nature of a diet supplement, the diet supplement may be consumed in any form. For instance, the dosage form of the diet supplement may be as a powder beverage mix, a liquid beverage, a ready-to-eat bar or drink product, a capsule, a tablet, a caplet, or as a dietary gel.

Furthermore, the dosage form of the diet supplement in accordance with these embodiments may be provided in accordance with customary processing techniques for herbal and/or diet supplements in any of the forms mentioned above.

In one embodiment of the present invention, which is set forth in greater detail in Example 1 below, a composition is provided for increasing the natural metabolic rate, burning calories, increasing thermogenesis and decreasing water retention.

In a second embodiment of the present invention, which is set forth in greater detail in Example 2 below, a composition is provided for increasing the natural metabolic rate, burning calories, increasing thermogenesis and decreasing water retention.

In a third embodiment of the present invention which is set forth in greater detail in Example 3 below, a composition is provided for decreasing water retention and stimulating diuretic effects to improve muscular definition.

The compositions according to the present invention may be employed in methods for increasing the natural metabolic rate, burning calories, increasing thermogenesis and decreasing water retention in subjects. The compositions of the present invention are particularly advantageous for athletes and bodybuilders to improve muscular definition. The dosage amount of the compositions according to the present invention which is administered to a subject may vary depending on the desired effect, the body weight and other characteristics of the subject. For example, in various embodiments, the compositions according to the present invention are administered to the subject on a daily basis. In another embodiment the compositions according to the present invention are administered to the subject three times daily.

The present invention also provides a method of increasing the natural metabolic rate, burning calories, increasing thermogenesis and decreasing water retention in a subject. In one embodiment, the methods of the present invention include administering a composition to a subject. According to another embodiment of the present invention, methods for reducing body fat mass leading to weight loss and thus improving visible muscular definition are provided. In one embodiment of the present invention, methods for decreasing water retention and enhancing diuretic effects, thereby improving muscular definition, are provided. In another embodiment, the administration of compositions according to the present invention allow a person's body to burn more calories than the person's body would otherwise burn (dramatically increasing thermogenesis), thereby reducing body fat mass leading to weight loss.

In example embodiments set forth below, the methods of the present invention provide for the administration of compositions according to the present invention that decrease water retention. For example, the administration of compositions according to the present invention may provide a diuretic effect causing a person to retain less water than the person would otherwise retain, thereby providing weight loss and improving muscular definition.

In embodiments described in the examples below, compositions and related methods comprising a first combination of one or more of *theobroma* extract, green tea extract, oolong tea extract, white tea extract, caffeine, niacin, and yerba maté extract, and guarana extract;

a second combination of one more of dandelion root extract, juniper berry powder, parsley powder (leaf), cayenne pepper powder, and xanthinol nicotinate;

a third combination of one or more of N-acetyl-L-tyrosine, *gynostemma pentaphyullum* extract, and vinpocetine. Additionally, the present invention may also comprise thiamin, pyridoxine, picamilone, *garcinia cambogia* extract, and/or xanthinol nicotinate.

The compositions according to the present invention may be administered in methods for increasing the natural metabolic rate, burning calories, increasing thermogenesis and decreasing water retention. The methods of the present invention are particularly advantageous for athletes and bodybuilders to improve visible muscular definition. In certain embodiments, the methods of the present invention include a determination, and an administration, of an amount of a composition in accordance with factors such as the desired effect, the body weight and characteristics of the athlete. For example, in certain embodiments, the present invention includes methods of administering compositions according to the invention to subjects on a daily basis or three times daily.

Although the following example illustrates the practice of the present invention in example embodiments, the examples should not be construed as limiting the scope of the invention. Other embodiments will be apparent to one skilled in the art from consideration of the specification and example.

Example 1

As a first example, the following composition is provided: green tea extract (0.4440 g), caffeine anhydrous (0.3000 g), dandelion root powder (0.2500 g), parsley powder (0.2000 g), juniper berry powder (0.2000 g), cayenne pepper powder (0.1000 g), n-acetyl-l-tyrosine (0.1000 g), quercetin dehydrate (0.1000 g), picamilone HCl (0.1000 g), *gynostemma pentaphyullum* leaf exact (0.0350 g), niacin (0.0330 g), oolong tea dry leaf extract (0.0100 g), white tea dry leaf extract (0.0100 g), *theobroma cocao* extract (0.0100 g), vinpocetine (0.0050 g), pyridoxine HCl (0.0020 g), thiamin mononitrate (0.0015 g), guarana powder (0.0010 g), yerba maté leaf powder (0.0010 g), gelatin, titanium dioxide, microcrystalline cellulose (0.0660 g), magnesium stearate (0.0330 g), and silica (0.0165 g).

The example composition may be ingested 30 to 60 minutes prior to eating a meal. The example composition can also be consumed prior exercise to increase and athlete's training intensity.

Example 2

As a second example, the following composition is provided: green tea extract (0.440 g), caffeine anhydrous (0.3000 g), dandelion root powder (0.2500 g), parsley powder (0.2000 g), juniper berry powder (0.200), cayenne pepper powder (0.100 g), n-acetyl-l-tyrosine (0.1000 g), quercetin dehydrate (0.1000 g), xanthinol nicotinate (0.1000 g), *gynostemma pentaphyullum* leaf exact (0.0350 g), niacin (0.0330 g), oolong tea dry leaf extract (0.0100 g), white tea dry leaf extract (0.0100 g), *theobroma cocao* extract (0.0100 g), vinpocetine (0.0050 g), pyridoxine HCl (0.0020 g), thiamin mononitrate (0.0015 g), guarana powder (0.0010 g), yerba maté leaf powder (0.0010), gelatin, titanium dioxide, microcrystalline cellulose (0.0660), magnesium stearate (0.0330 g), and silica (0.0165 g).

The example composition may be ingested 30 to 60 minutes prior to eating a meal. The example composition can also be consumed prior exercise to increase and athlete's training intensity.

Example 3

As a third example, the following composition is provided: Dandelion Root Powder (0.3000 g), Parsley Powder (0.2000 g), N-Acetyl-L-Tyrosine (0.1000 g), Burdock Root Extract (0.0500 g), Picamilone HCl (0.0500 g), Licorice Root Extract (0.0100 g), Vinopcetine (0.0050 g), Quercetin Dihydrate (0.0020 g), Artichoke Powder (0.0020 g), *Gynostemma Pentphyullum* (0.0010 g), and Buchu Leaf Extract (0.0010 g).

As part of a kit designed to aid in the building of muscle, fat loss and improvement of muscular definition, the composition may be ingested at least once daily during the last week of a three week supplement regimen.

What is claimed is:

1. A method for decreasing water retention and stimulating diuretic effects in a subject in need thereof comprising administering to the subject an effective amount of a composition comprising dandelion powder, N-acetyl-L-tyrosine, *Gynostemma pentaphyllum*, picamilone, and quercetin dihydrate.

2. A method for decreasing water retention and stimulating diuretic effects in a subject in need thereof comprising administering to the subject an effective amount of a composition comprising dandelion powder, N-acetyl-L-tyrosine, *Gynostemma pentaphyllum*, picamilone, 0.2000 g of parsley powder; 0.0500 g of burdock root extract; 0.0100 g of licorice root extract; 0.0050 g of vinpocetine; 0.0020 g of quercetin dihydrate; 0.0020 g of artichoke powder; and 0.0010 g of buchu leaf extract.

* * * * *